(12) United States Patent
Sibary et al.

(10) Patent No.: US 8,792,999 B2
(45) Date of Patent: Jul. 29, 2014

(54) IMPLANTABLE TISSUE STIMULATING ELECTRODE ASSEMBLY

(75) Inventors: Peter Sibary, Luddenham (AU); Nicholas Pawsey, North Ryde (AU)

(73) Assignee: Cochlear Limited, Macquarie University NSW (AU)

( * ) Notice: Subject to any disclaimer, the term of this patent is extended or adjusted under 35 U.S.C. 154(b) by 0 days.

(21) Appl. No.: 13/357,790

(22) Filed: Jan. 25, 2012

(65) Prior Publication Data

US 2013/0190853 A1 Jul. 25, 2013

(51) Int. Cl.
*A61N 1/05* (2006.01)

(52) U.S. Cl.
USPC .............. 607/137; 607/55; 607/56; 607/136

(58) Field of Classification Search
USPC ..................... 607/137, 55, 56, 136
See application file for complete search history.

(56) References Cited

U.S. PATENT DOCUMENTS

| | | | |
|---|---|---|---|
| 5,545,219 A | 8/1996 | Kuzma | |
| 5,578,084 A | 11/1996 | Kuzma et al. | |
| 6,129,753 A * | 10/2000 | Kuzma | 607/137 |
| 7,367,992 B2 | 5/2008 | Dadd | |
| 7,937,154 B2 | 5/2011 | Risi | |
| 2009/0076581 A1 | 3/2009 | Gibson | |

FOREIGN PATENT DOCUMENTS

WO WO 2011103530 A2 * 8/2011

OTHER PUBLICATIONS

International Search Report and Written Opinion for International Application No. PCT/IB2013/050630 mailed Jun. 26, 2013 (13 pages).

* cited by examiner

*Primary Examiner* — Christopher D Koharski
*Assistant Examiner* — Michael Carey
(74) *Attorney, Agent, or Firm* — K&L Gates, LLP

(57) ABSTRACT

An electrode assembly including a carrier section, an electrode section(s), and joint section(s). Each electrode section including an electrode contact, and an electrode section body. Each joint section connecting the carrier section to at least one electrode section, and providing each connected electrode section with at least one of pitch, roll, and yaw about a point generally along an axis between the carrier section and the electrode section. The joint section made of material of durometer less the durometer of the carrier section. A fill section can substantially occupying the space between the carrier section and the electrode section that is not occupied by the joint section.

33 Claims, 12 Drawing Sheets

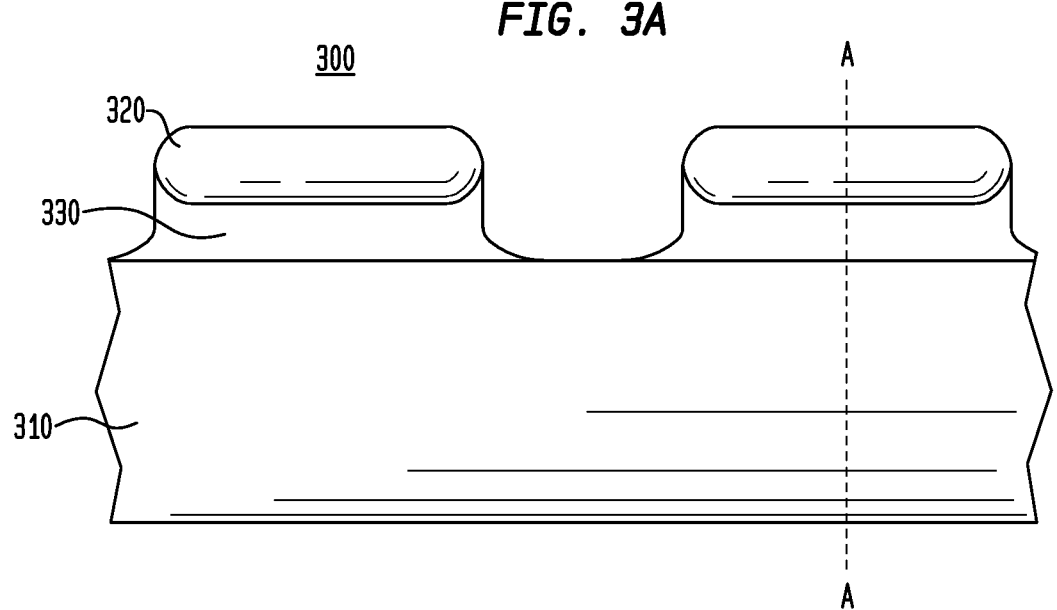
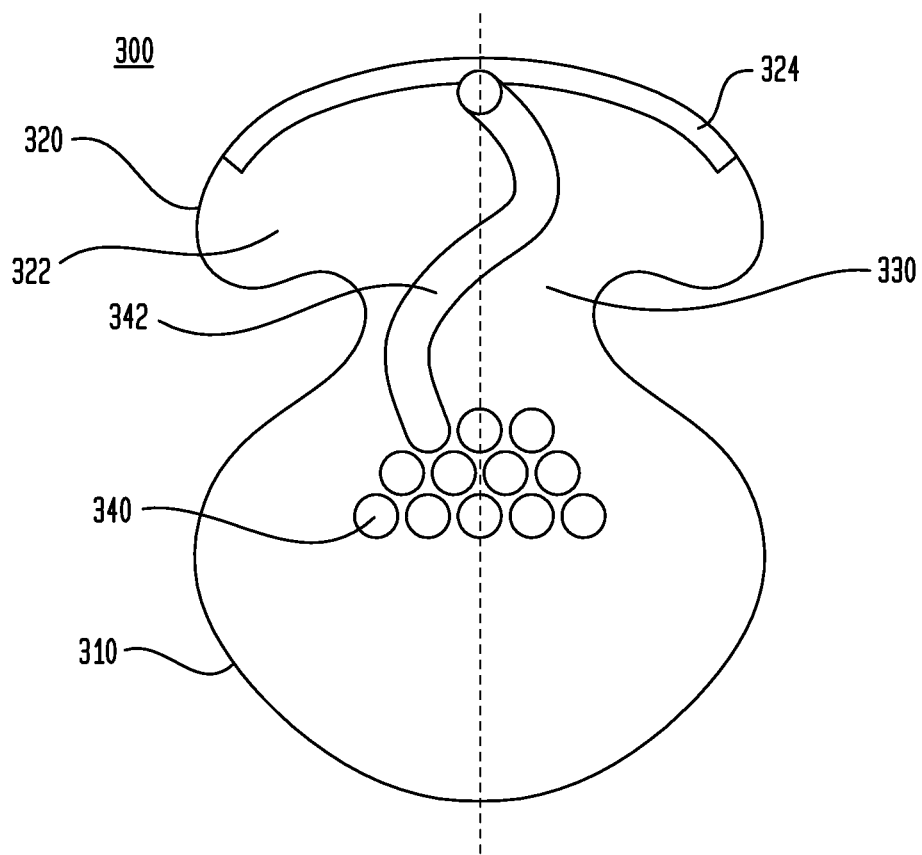

IMPLANTABLE TISSUE STIMULATING ELECTRODE ASSEMBLY

BACKGROUND

1. Field

The disclosed technology relates generally to implantable medical devices, and more particularly, to implantable medical devices including an implantable electrode assembly.

2. Related Art

A variety of implantable medical devices have been proposed to deliver controlled electrical stimulation to a region of a subject's body to achieve a therapeutic effect. Such devices, generally referred to herein as stimulating medical devices, include muscle or tissue stimulators, brain stimulators (deep brain stimulators, cortical stimulators, etc.), cardiac pacemakers/defibrillators, functional electrical stimulators (FES), spinal cord stimulators (SCS), pain stimulators, stimulating hearing prostheses, etc. Such stimulating medical devices include one or more electrode contacts that deliver electrical stimulation signals to the subject (commonly referred to as a patient, recipient, etc.; "recipient" herein). In addition, the stimulating medical devices may also include one or more electrode contacts to monitor and/or measure a particular biological activity, sometimes broadly referred to as sensors.

Hearing loss, which may be due to many different causes, is generally of two types, conductive and sensorineural. In some cases, a person suffers from hearing loss of both types. Conductive hearing loss occurs when the normal mechanical pathways for sound to reach the cochlea, and thus the sensory hair cells therein, are impeded, for example, by damage to the ossicles. Individuals who suffer from conductive hearing loss typically have some form of residual hearing because the hair cells in the cochlea are undamaged. As a result, individuals suffering from conductive hearing loss typically receive an acoustic hearing aid that generates mechanical motion of the cochlea fluid.

In many people who are profoundly deaf, however, the reason for their deafness is sensorineural hearing loss. Sensorineural hearing loss occurs when there is damage to the inner ear, or to the nerve pathways from the inner ear to the brain. As such, those suffering from some forms of sensorineural hearing loss are thus unable to derive suitable benefit from hearing prostheses that generate mechanical motion of the cochlea fluid. As a result, medical devices having one or more implantable components that deliver electrical stimulation signals to a patient or recipient have been developed. Certain such implantable medical devices include an array of stimulating electrode contacts that deliver the stimulation signals to nerve cells of the recipient's auditory system, thereby providing the recipient with a hearing percept.

As used herein, the recipient's auditory system includes all sensory system components used to perceive a sound signal, such as hearing sensation receptors, neural pathways, including the auditory nerve and spiral ganglion, and parts of the brain used to sense sounds. Electrically-stimulating implantable medical devices include, for example, auditory brain stimulators and cochlear prostheses (commonly referred to as cochlear prosthetic devices, cochlear implants, cochlear devices, and the like; simply "cochlear implants" herein).

Oftentimes sensorineural hearing loss is due to the absence or destruction of the cochlear hair cells that transduce acoustic signals into nerve impulses. It is for this purpose that cochlear implants have been developed. Cochlear implants provide a recipient with a hearing percept by delivering electrical stimulation signals directly to the auditory nerve cells, thereby bypassing absent or defective hair cells that normally transduce acoustic vibrations into neural activity. Such devices generally use an electrode array implanted in the cochlea so that the electrodes may differentially activate auditory neurons that normally encode differential pitches of sound.

SUMMARY

The disclosed technology comprises devices that include a carrier section, an electrode section, and a joint section. The electrode section includes an electrode contact, and an electrode section body. The joint section connects the carrier section to at least one electrode section, and provides each connected electrode section with at least one of pitch, roll, and yaw about a point generally along an axis between the carrier section and the electrode section. In various embodiments, the joint section comprises material of durometer less the durometer of one or both of the carrier section and the electrode section. Some embodiments further include a fill section. The fill section can substantially occupy the space between the carrier section and the electrode section that is not occupied by the joint section. The fill section can be made of material of durometer less than the durometer of the joint section. The device further can include one or more conductive pathways connected to each electrode contact. Some embodiments of the technology include a biasing member biasing the carrier section generally toward the joint section. In various embodiments, the carrier section is characterized by a substantially constant diameter along its longitudinal axis. Methods of the technology include inserting an electrode assembly as described above into the cochlea via at least one of: a cochleostomy, the round window, the oval window, and the promontory or opening in an apical turn of the cochlea.

DESCRIPTION OF THE DRAWINGS

Embodiments of the disclosed technology are described below with reference to the attached drawings, in which:

FIG. 3A is a longitudinal section of an electrode assembly in accordance with embodiments of the present technology;

FIG. 3B is a cross section of an electrode assembly, in accordance with embodiments of the present technology;

Figure 1:
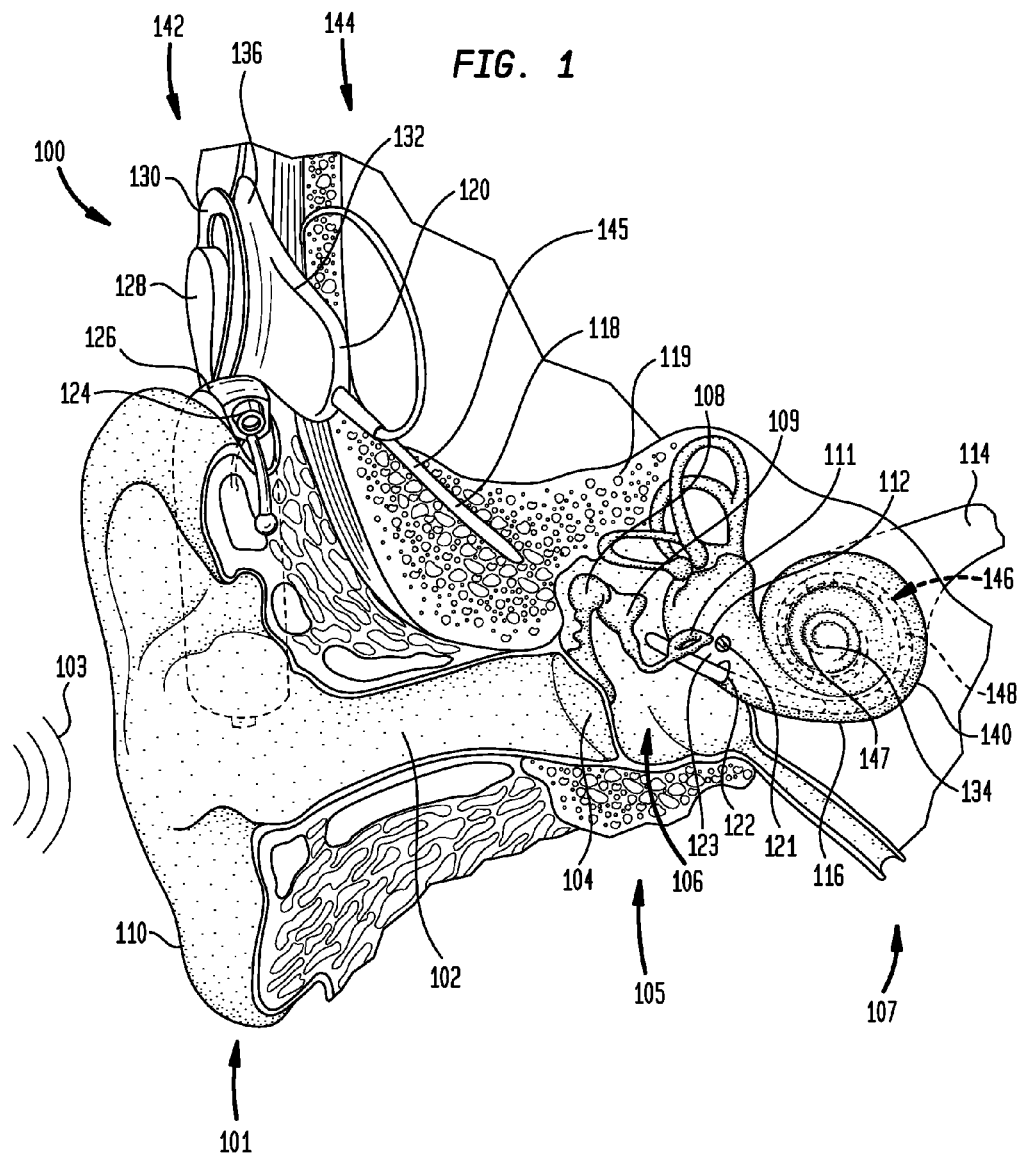
FIG. 1 is a perspective view of an exemplary stimulating medical device, a cochlear implant, having an electrode assembly in accordance with embodiments of the present technology.

Some features in the drawings are not to scale, and have been tailored to better illustrate the technology.

DETAILED DESCRIPTION

Embodiments are described herein primarily in connection with one type of stimulating medical device, a cochlear implant. Cochlear implants are hearing prostheses that deliver electrical stimulation, alone or in combination with other types of stimulation, to the cochlea of a recipient. It would be appreciated that embodiments of the present technology can be implemented in any cochlear implant or stimulating medical device now know or later developed. Some embodiments of the disclosed technology can find use in the treatment of tinnitus.

FIG. 1 is a perspective view of an exemplary cochlear implant 100 implanted in a recipient having an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 that vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate, in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 that is directly or indirectly attached to the body of the recipient, and an internal or implantable component 144 that is temporarily or permanently implanted in the recipient.

External component 142 typically comprises one or more sound input elements, such as microphone 124 for detecting sound, a sound processing unit 126, a power source (not shown), and an external transmitter unit 128. External transmitter unit 128 comprises an external coil 130, and preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an elongate stimulating lead assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. Internal coil 136 receives power and stimulation data from external coil 130, as noted above. Elongate stimulating lead assembly 118 has a proximal end connected to stimulator unit 120, and extends through mastoid bone 119. Lead assembly 118 has a distal region, referred to as electrode assembly 145, implanted in cochlea 140. As used herein the term "stimulating lead assembly," refers to any device capable of providing stimulation to a recipient, such as, for example, electrical or optical stimulation.

Electrode assembly 145 may be implanted at least in basal region 116 of cochlea 140, and sometimes further. For example, electrode assembly 145 may extend towards apical end of cochlea 140, referred to as cochlea apex 134. Electrode assembly 145 may be inserted into cochlea 140 via a cochleostomy 122, or through round window 121, oval window 112, and the promontory 123 or opening in an apical turn 147 of cochlea 140.

Electrode assembly 145 has disposed therein or thereon a longitudinally aligned and distally extending array 146 of electrode contacts 148, sometimes referred to as electrode array 146 herein. Throughout this description, the term "electrode array" means a collection of two or more electrode contacts, sometimes referred to simply as contacts herein. As used herein, electrode contacts or other elements disposed in a carrier refer to elements integrated in, or positioned on, the carrier member. As such, electrode array 146 is referred to herein as being disposed in electrode assembly 145. Stimulator unit 120 generates stimulation signals which are applied by electrodes 148 to cochlea 140, thereby stimulating auditory nerve 114.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

As noted, FIG. 1 illustrates a context of the present technology in which cochlear implant 100 includes an external component 142. It would be appreciated that in alternative embodiments, cochlear implant 100 comprises a mostly-implantable or totally implantable device. A totally implantable prosthesis that is capable of operating, at least for a period of time, without the need of an external component. In such embodiments, all components of cochlear implant 100 are implantable, and the cochlear implant operates in conjunction with external component 142.

Figure 2:
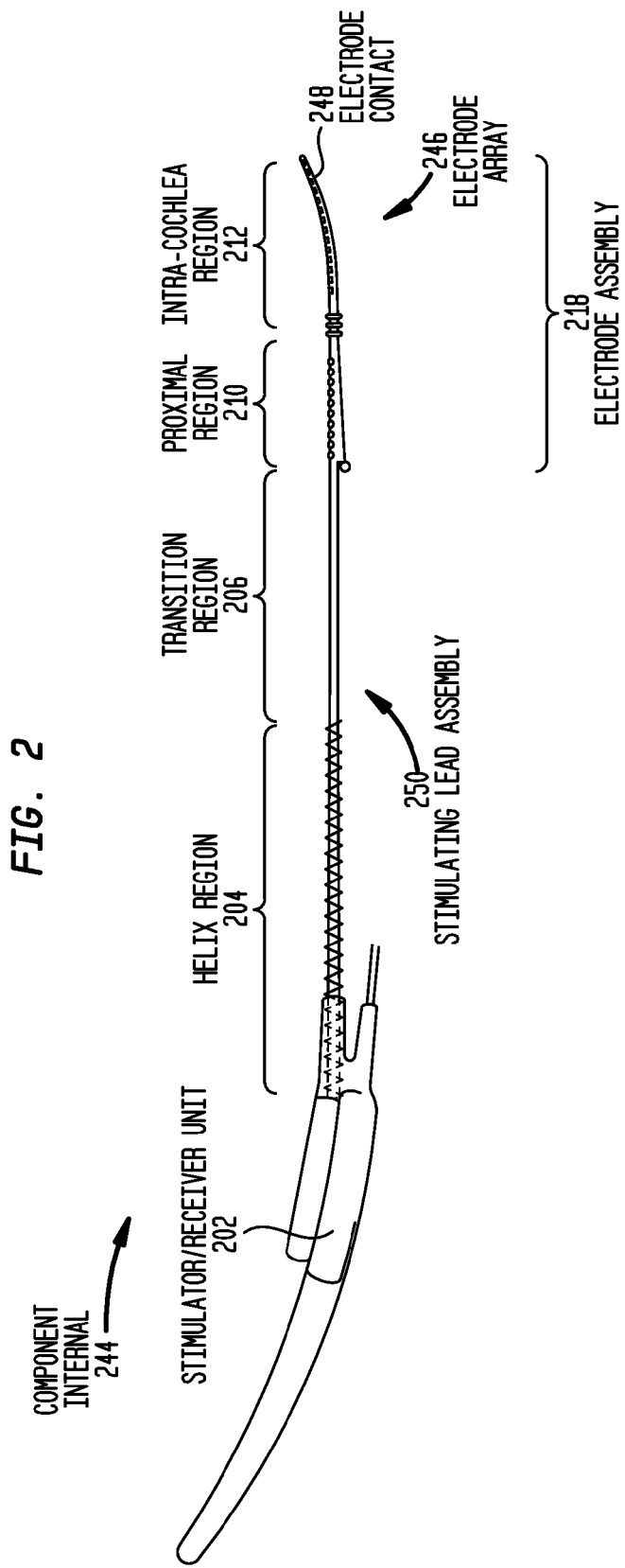
FIG. 2 is a side view of a conventional implantable component of a cochlear implant.

FIG. 2 is a simplified side view of an embodiment of internal component 144, referred to herein as internal component 244. As shown in FIG. 2, internal component 244 comprises a stimulator/receiver unit 202, which, as described above, receives encoded signals from an external component of the cochlear implant. Connected to stimulator/receiver unit 202 is a stimulating lead assembly 250. Stimulating lead assembly 250 terminates in an electrode assembly 218 that comprises a proximal region 210 and an intra-cochlear region 212. Intra-cochlear region 212 is configured to be implanted in the recipient's cochlea and has disposed thereon an array 246 of conventional electrode contacts 248. Proximal region 210 is configured to be positioned outside of the recipient's cochlea.

In certain embodiments, electrode assembly 218 is configured to adopt a curved configuration during or after implantation into the recipient's cochlea. To achieve this, in certain embodiments, electrode assembly 218 is pre-curved to the same general curvature of a cochlea. In such embodiments, electrode assembly 218 is referred to as perimodiolar electrode assembly that is held straight by, for example, a stiffening stylet (not shown) or sleeve (or combination of both), which is removed during implantation so that the electrode assembly may adopt its curved configuration when in the cochlea. Other methods of implantation, as well as other electrode assemblies that adopt a curved configuration, may be used in embodiments of the present technology.

In other embodiments, electrode assembly 218 is a non-perimodiolar electrode assembly that does not adopt a curved configuration. For example, electrode assembly 218 may comprise a straight electrode assembly or a mid-scala assembly that assumes a mid-scala position during or following implantation.

In the illustrative embodiments of FIG. 2, stimulating lead assembly 250 further comprises a helix region 204 and a transition region 206 connecting stimulator/receiver unit 202 to electrode assembly 218. Helix region 204 prevents the connection between stimulator/receiver 202 and electrode assembly 218 from being damaged due to movement of internal component 244 which may occur, for example, during mastication.

Figure 3C:
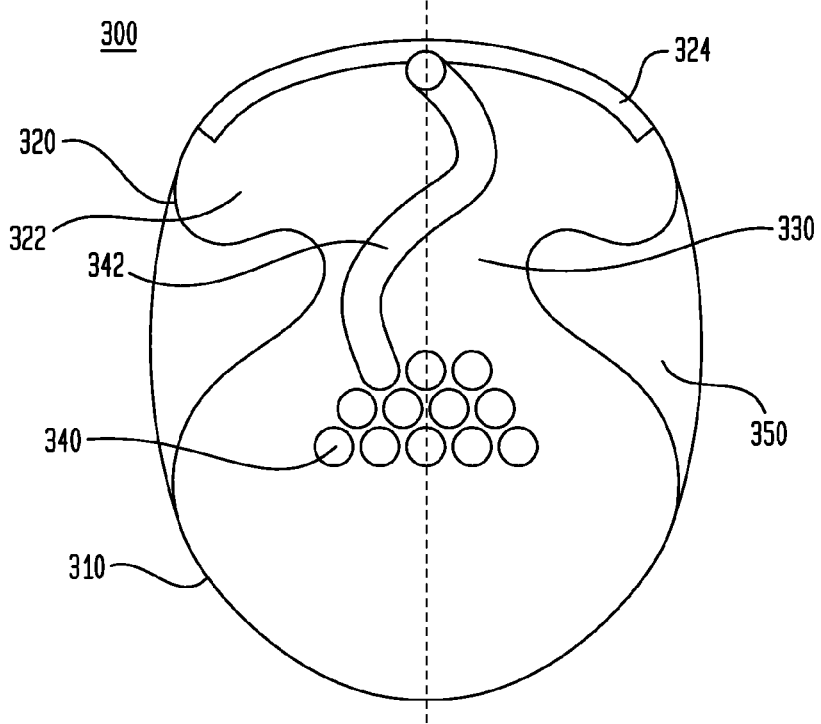
FIG. 3C and FIG. 3D are each a cross section of an electrode assembly, in accordance with embodiments of the present technology, comprising a fill section between the carrier body and the electrode body, and surrounding the joint.
Figure 3D:
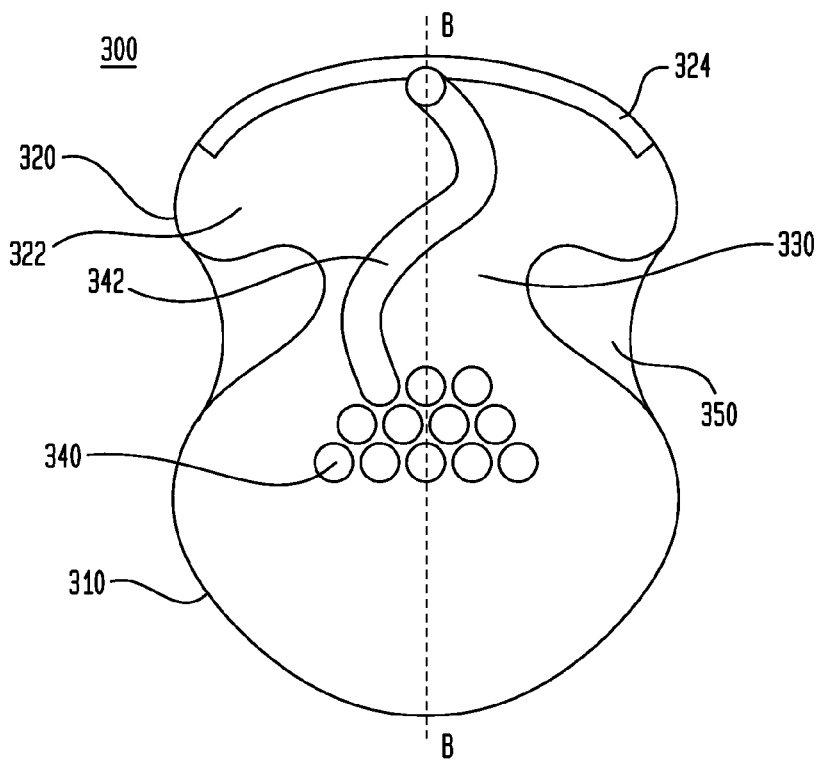

Referring to FIG. 3, both a longitudinal section (FIG. 3A), and cross sections (FIGS. 3B and 3C) along line A-A of an electrode assembly 300 of the present technology are shown. The electrode assembly can be part of the internal component 244 of a cochlear implant 100 as described above in reference to FIG. 1 and FIG. 2. A carrier section 310 forms a longitudinal base for the electrode assembly. At least one electrode section 320 can be connected to the carrier section 310 via a joint section 330.

Embodiments of the present technology include tissue-stimulating electrode assemblies wherein each electrode section 320 is connected to a carrier section 310 by a joint section 330 that allows at least one degree of freedom in positioning electrode contacts more advantageously in relation to a stimulation site.

The carrier section 310 can be formed substantially of medical-grade silicone of durometer generally in the range of 30 to 90 (Shore Type "A"). In some embodiments of the present technology, e.g., those implanted using a stylet insertion tool, a lumen (not show) can be formed in the carrier section, e.g., to accommodate the stylet. In those embodiments, a sheath insertion tool is not needed. Other embodiments of the technology can use a combination of sheath insertion tool, stylet insertion tool, and other biasing/stiffening members (including biasing/stiffening members that dissolve when exposed to body fluids). In some embodiments of the technology, the carrier section can include a biasing member (not shown) that biases the carrier section 310 generally toward the modiolar wall.

The electrode section 320 can comprise an electrode section body 322 and at least one electrode contact 324. Each contact 324 can be electrically connected to at least one conductive pathway connected between the contact 324 and a stimulator/receiver unit 202 (e.g., in those embodiments where the electrode assembly 300 is part of a stimulating lead assembly 250)—via the electrode section body 322, the connecting joint section 330, and the carrier section 310. FIG. 3B illustrates several conductive pathways, with one conductive pathway 340 connecting to contact 324. The connecting conductive pathway includes a strain relief 342, such as the strain relief disclosed in U.S. Pat. App. Pub. No. 2001/0152991. Conductive pathways can be single wires; however, it should be appreciated that in accordance with embodiments of the present technology, conductive pathways can comprise, for example, multi-strand wires or may comprise cut, punched, or machined foil strips of platinum, platinum iridium alloy, or other material including carbon nanotubes or fiber optic connections.

The electrode section body 322 can be formed substantially of any suitable material including silicone, polyurethanes or other body compatible polymeric materials suitable for the intended application and use. In some embodiments, the electrode section body 322 is formed of the same material as the carrier section 310.

Electrode contacts 324 are preferably made from platinum, but any other suitable material such as iridium, a platinum/iridium alloy, or carbon nanotubes, may be used as will be understood by a person skilled in the art. Electrode contacts 324 can be substantially planar and have a rectangular shape. However, it should be appreciated that electrode contacts 324 may have other shapes, such as, for example, a U-shape, square, circular, oval, etc. In some embodiments, electrode contact 324 is flexible for, inter alia, increased compliance with variations in the implant surface.

The joint section 330 can allow at least one of pitch, roll, and yaw between each electrode section 320 and the carrier body 310, preferably along a point substantially along an axis between the two, e.g., along B-B. In some embodiments, the joint section 330 allows compression substantially along the B-B axis. The joint section 330 can be formed substantially of medical-grade silicone of durometer generally in the range of 15 to 60 (Shore Type "A"). In some embodiments of the technology, the durometer of the joint section is less than the durometer of the carrier body 310.

FIG. 3C illustrates embodiments of the present technology in cross section that include a fill section 350. Fill section 350 can occupy some or all of the space between the electrode section 320 and the carrier body 310 that is not occupied by the joint section 330. In some embodiments, the fill section is made of material of substantially less durometer that any of the joint section 330, the electrode section 320, and the carrier section 310. For example, the fill section 350 can be formed from medical-grade silicone of durometer generally in the range of 15 to 30 (Shore Type "A"). Use of a fill section, such as section 350, can allow the external profile of the electrode array to be substantially continuous, e.g., without cavities or other indented regions while still allowing the joint section to perform its function, e.g., allowing the electrode section at least one degree of freedom of movement with respect to the carrier section. A continuous profile can also facilitate robustness of the joint section, and can facilitate explantation. The fill section 350 can be used to reduce the risk of bacterial growth, and can be used as a carrier for drugs.

In some embodiments, one or more of the carrier body, electrode section, joint section, and fill section are unitary members with the durometer of the material constant or varying as described above across regions of the electrode assembly that would otherwise constitute discrete elements.

Figure 4:
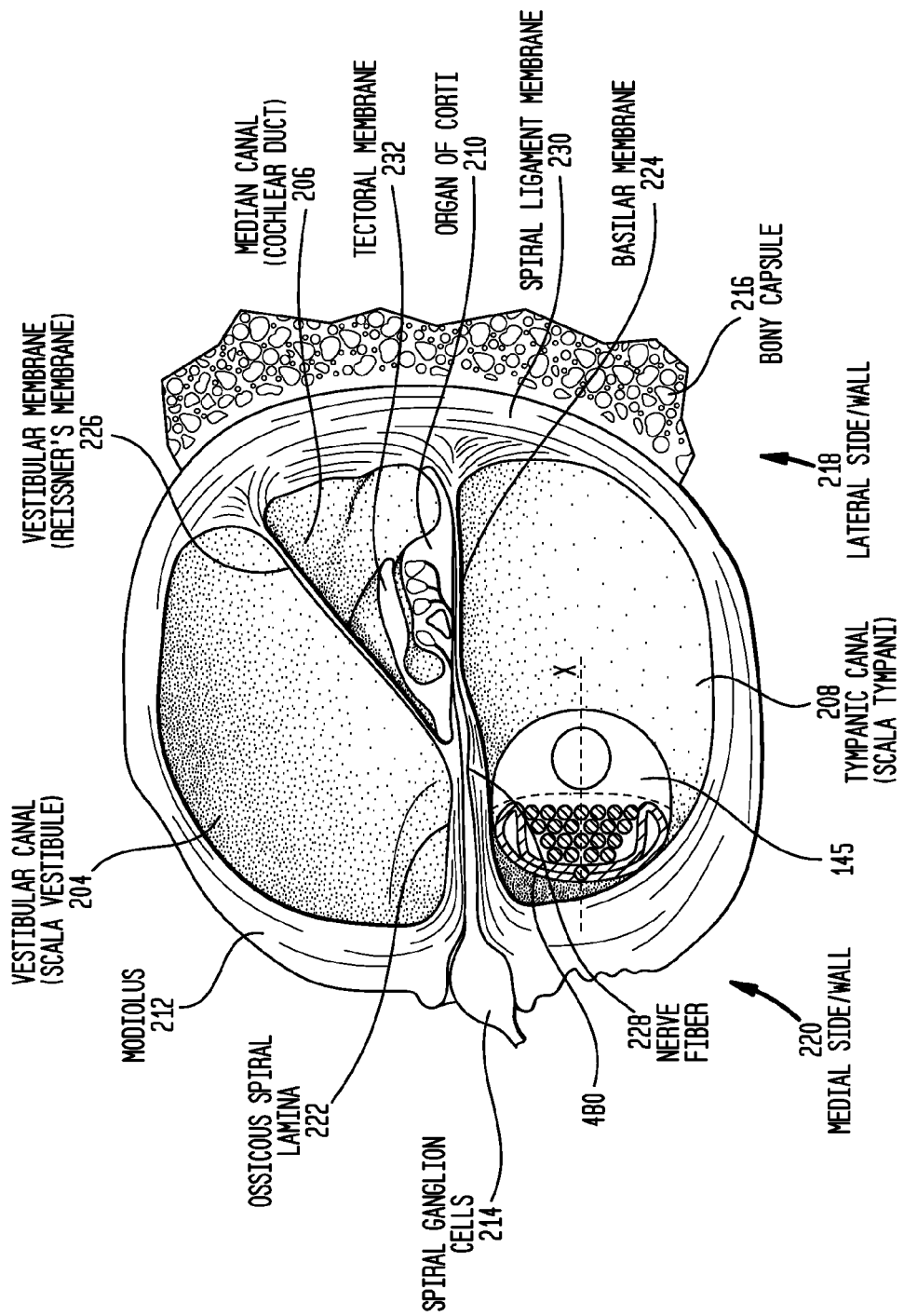
FIG. 4 is a cross-sectional view of a conventional electrode assembly having an electrode body with orientation directed to a modiolar wall.

For a perimodiolar cochlear implant, the contacts of the electrode assembly are generally facing toward a recipient's modiolus. In FIG. 4, a perimodiolar electrode assembly 145 is shown in cross section in the scala tympani 208 of a recipient's cochlea 140. This electrode assembly 145 includes the contact and conductive pathways in its carrier section, and does not include a joint section or electrode section. When biased toward the modiolar wall on the medial side 220 of the scala tympani, this electrode assembly, maintaining its X-Y orientation as shown, makes less than ideal contact with the modiolar wall (as illustrated by gap 480).

Figure 5:
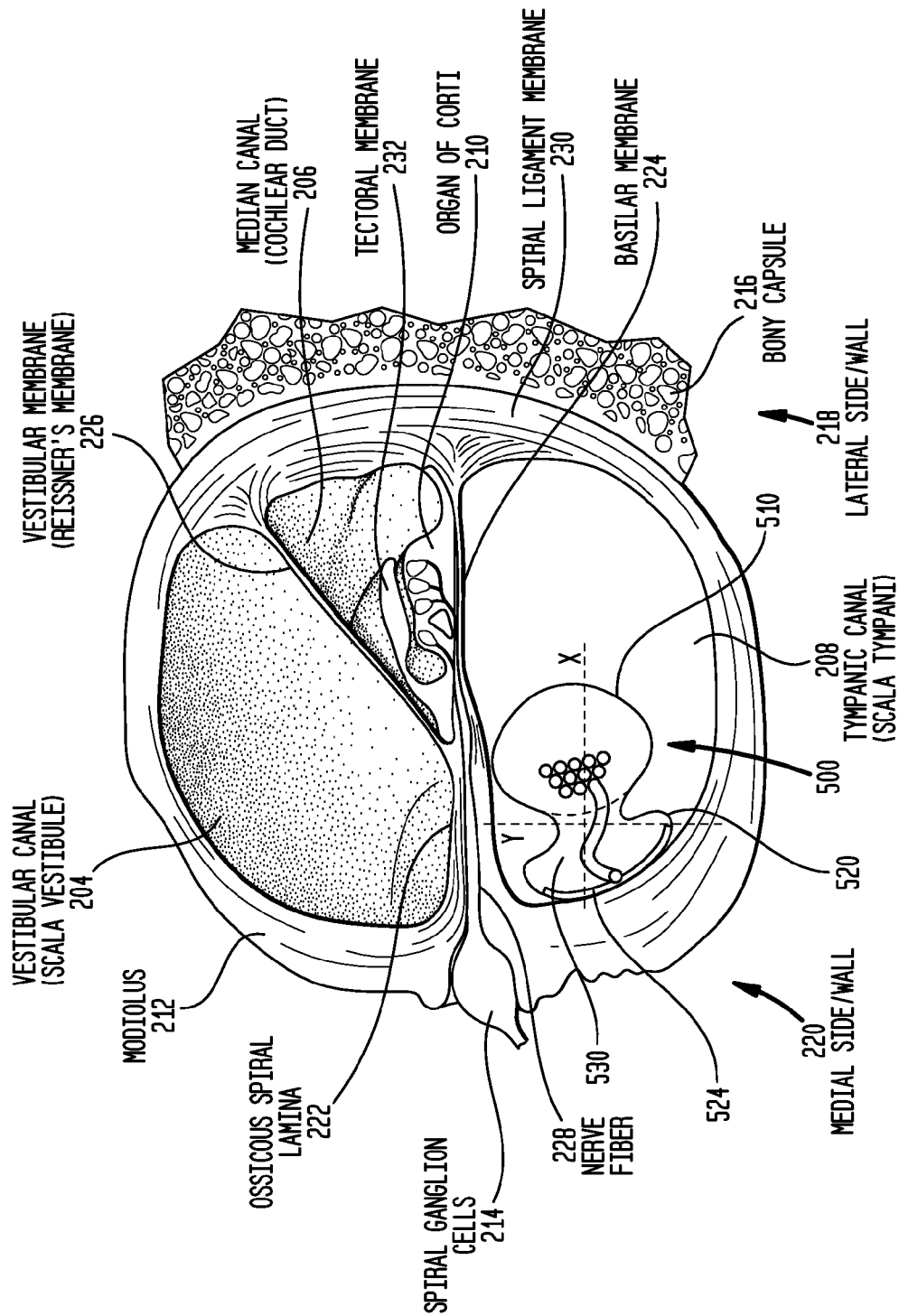
FIG. 5 is a cross-sectional view of an electrode assembly of the present technology having an electrode body with orientation directed to a modiolar wall, in accordance with embodiments of the present technology.

In FIG. 5, an electrode carrier 500 of the present technology is shown in cross section in the scala tympani 208 of a recipient's cochlea 140. When this electrode carrier 500 is biased toward the modiolar wall on the medial side of the scala tympani, the freedom of movement provided by the joint section 530 allows the electrode section 520 (and more specifically, the electrode contact 524) to be more favorably oriented to the modiolar wall, as indicated by the lack of a gap such as the gap 480 illustrated in FIG. 4. Note that carrier body 510 of the present technology maintains substantially the same orientation as electrode assembly 145 in FIG. 3D. In some embodiments, motion along the B-B axis is allowed, e.g., compression of the joint section 530. In some embodiments, compression of the joint section may allow the array to accommodate variations in the modiolar wall to prevent the electrode sitting on the high points of the spiral, allowing more of the electrodes to be in contact with the wall, and more evenly distributing the contact pressure.

Figure 6:
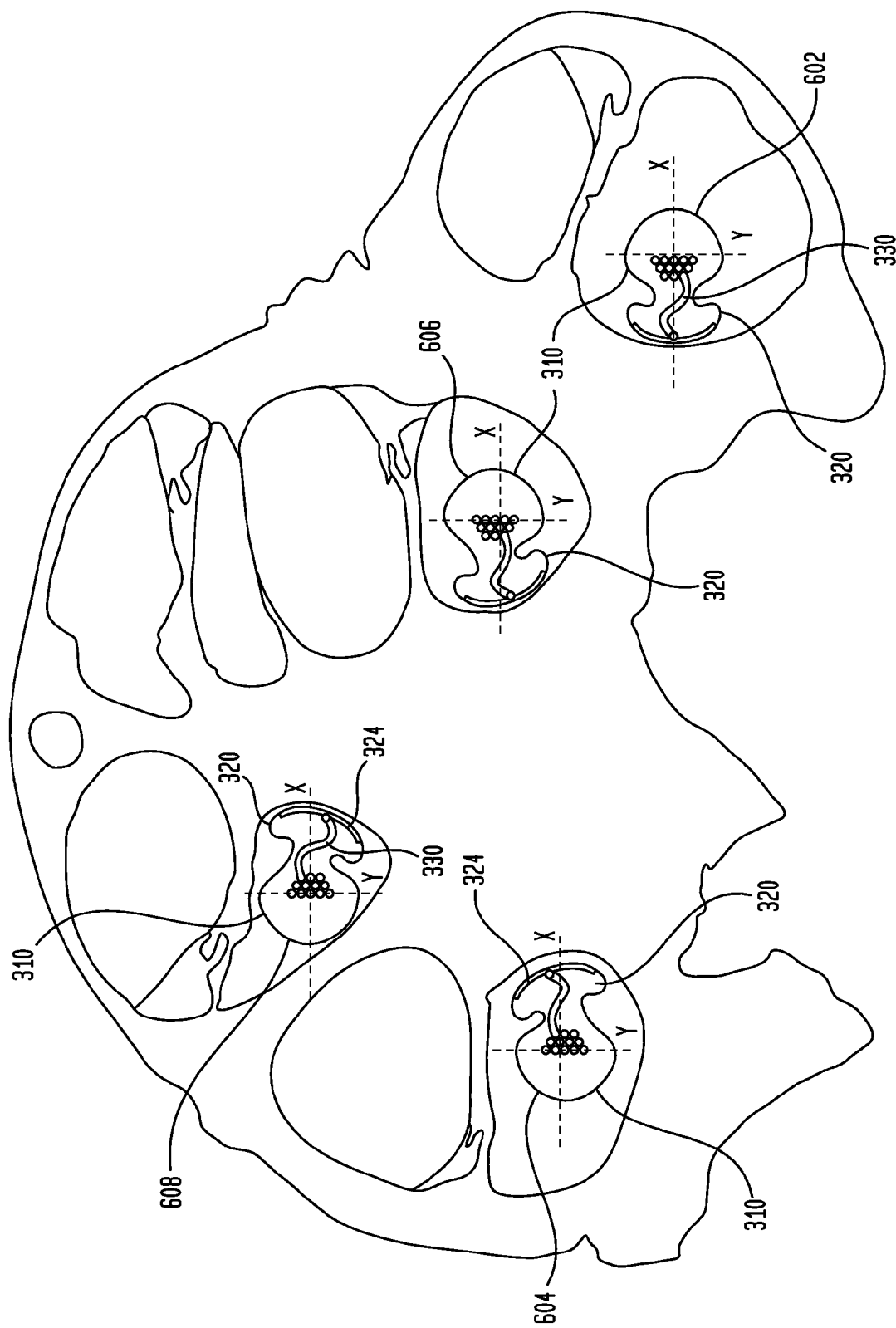
FIG. 6 a cross-sectional view of a cochlea with an implanted electrode carrier member illustrating the electrodes being compliant with a modiolar wall in the illustrated plane.

FIG. 6 is an outline representation of a computed tomography scan of a cross section of a cochlea, an electrode assembly 600 of the present technology implanted therein. In FIG. 6, four (4) cross sections 602, 604, 606, and 608 (in order from most basal to most apical), of electrode assembly 600 are shown. Carrier body 310 maintains substantially the same orientation, as indicated by axes X and Y in each cross-section 602, 604, 606 and 608. However, the orientation of electrode section 320 with respect to the carrier section 310 and joint section 330 changes for positioning of electrode contact 324 against the modiolar wall. In general, each electrode section has at least one degree of freedom to adopt a position against the modiolar wall.

Movement between the carrier section 310 and the electrode section 320 through flexing of the joint section 330 in dimensions other than those shown in FIG. 6 is provided for by embodiments of the present technology, however such movement is not explicitly shown in FIG. 6 due to the two-dimensional nature of the figure.

Figure 10:
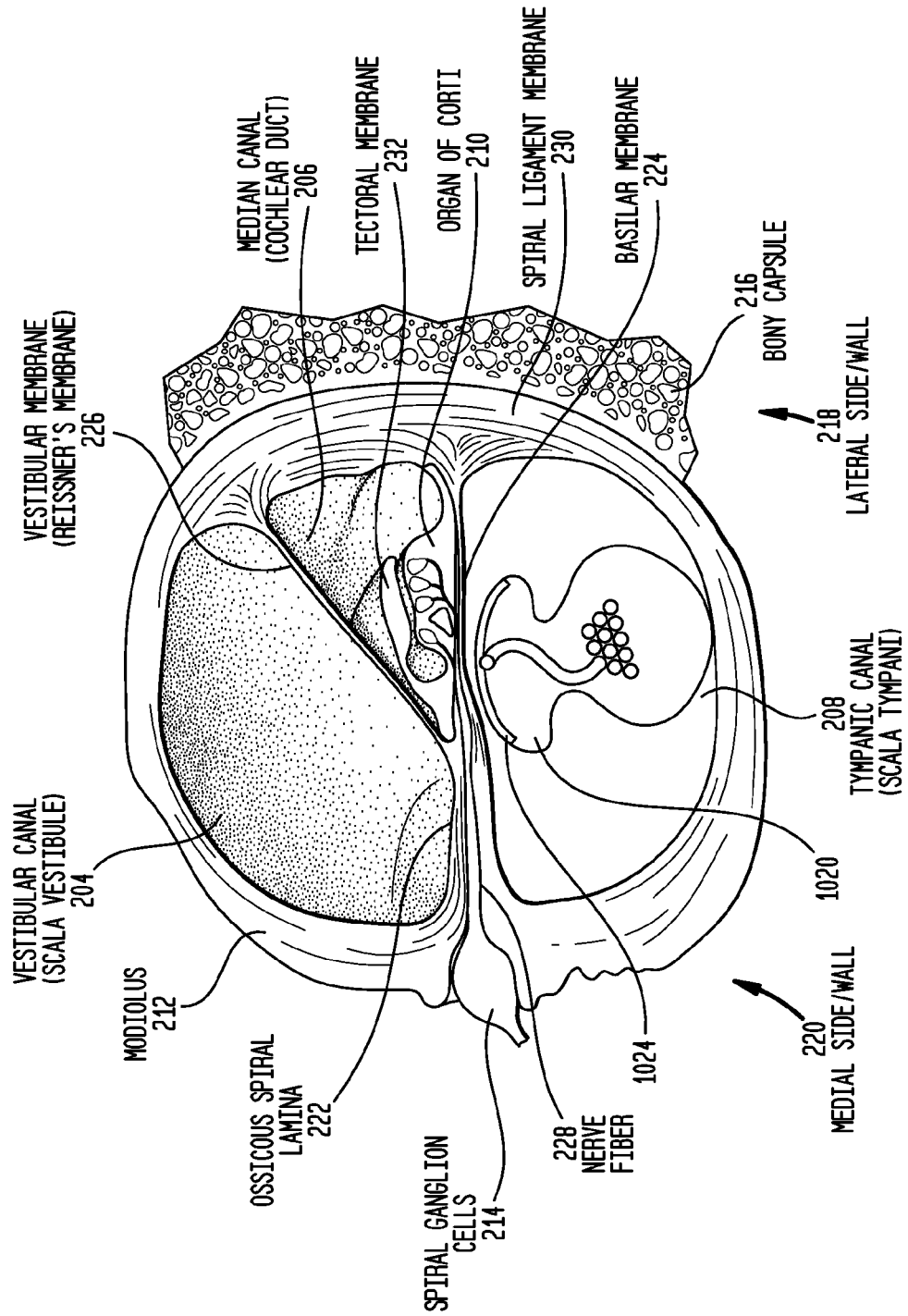
FIG. 10 is a cross-sectional view of an electrode assembly of the present technology having an electrode body with orientation directed to a basilar membrane, in accordance with embodiments of the present technology.

Referring to FIG. 10 an electrode carrier of the present technology is shown in cross section in the scala tympani 208 of a recipient's cochlea 140. When this electrode carrier is biased toward the basilar membrane 224 of the scala tympani 208, the freedom of movement provided by the joint section 1030 allows the electrode section 1020 (and more specifically, the electrode contact 1024) to be more favorably oriented to the basilar membrane.

Figure 11:
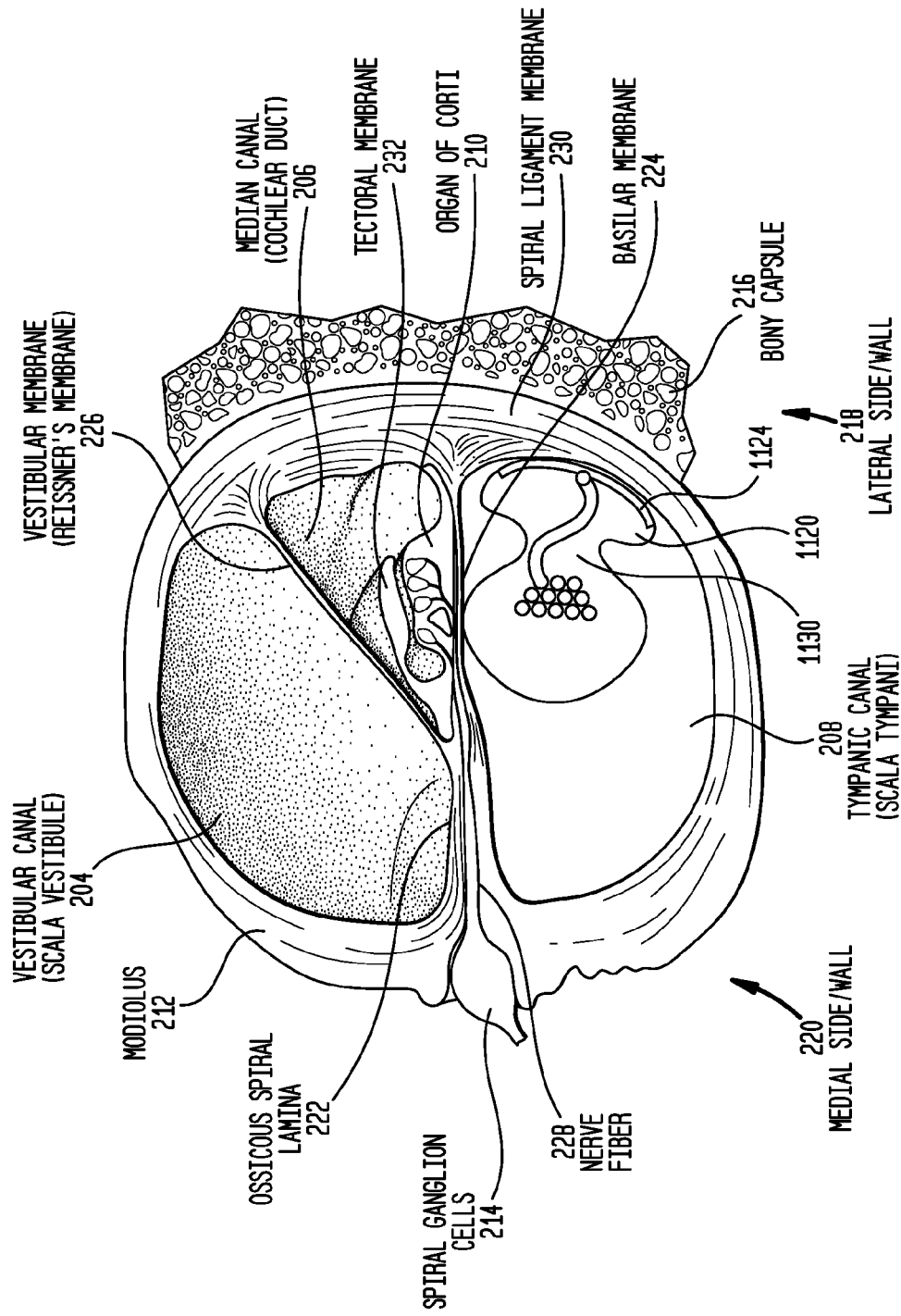
FIG. 11 is a cross-sectional view of an electrode assembly of the present technology having an electrode body with orientation directed to the lateral side of the scala tympani, in accordance with embodiments of the present technology.

Referring to FIG. 11 an electrode carrier of the present technology is shown in cross section in the scala tympani 208 of a recipient's cochlea 140. When this electrode carrier is biased toward the lateral side 218 of the scala tympani 208, the freedom of movement provided by the joint section 1130 allows the electrode section 1120 (and more specifically, the electrode contact 1124) to be positioned against the lateral side 218 of the scala tympani 208.

The freedom of movement offered by an electrode assembly of the present technology can lead to the surface area of the electrode contact 324 being more proximate to the stimulation site, and can allow the electrode assembly 300 to adapt to variation (across recipients) and non-uniformities (within a recipient) in the tissue surface at the electrode site.

As a result, lower current levels may be used to evoke the same hearing percept in a recipient. Smaller (and more numerous) electrodes may be used for greater tonotopic resolution, and without increasing charge density (i.e., lower current levels) to evoke the same percept.

In a conventional perimodiolar electrode assembly, the size of electrodes decreases from the basal end of the electrode assembly to the apical end of the electrode assembly. Since the electrodes are typically coextensive with a portion of the circumference of the typically circular cross section electrode assembly, the diameter of the electrode assembly also decreases from its basal end to its apical end.

Consider a sheath insertion tool. The end of a sheath insertion tool is typically placed at the basal turn of the cochlea and the electrode assembly is pushed out of the sheath until the electrode assembly is inserted to its desired depth, at which point, the end of the sheath insertion tool is occupied by the largest diameter of the electrode assembly that will pass the end of the insertion tool.

This requires the sheath insertion tool to have an inner diameter at its end point that accommodates this largest diameter. However, prior to insertion, the end of the sheath insertion tool is occupied by the smallest diameter portion of the electrode, i.e., the most-apical portion.

Given that a perimodiolar electrode assembly is curved, the difference in diameter between the apical end of the electrode assembly and inner diameter of the end of the sheath insertion tool presents an opportunity for the tip of the electrode assembly to be damaged, and for undesirable positioning, for example, twist to be introduced into the electrode assembly.

The present technology allows the use of electrode assemblies that have substantially constant diameter along the portion of the carrier member that will pass the end of a sheath insertion tool. This can reduce, if not eliminate, the difference between the diameter of the apical end of the electrode assembly and the inner diameter of the sheath insertion tool—thereby reducing the opportunity for damage to the electrode assembly tip and for the introduction of undesirable positioning such as twist into the electrode assembly. Reducing the undesirable positioning in the electrode when it is being held straight can lead to more consistent outcomes during insertion into the cochlea.

Figure 7:
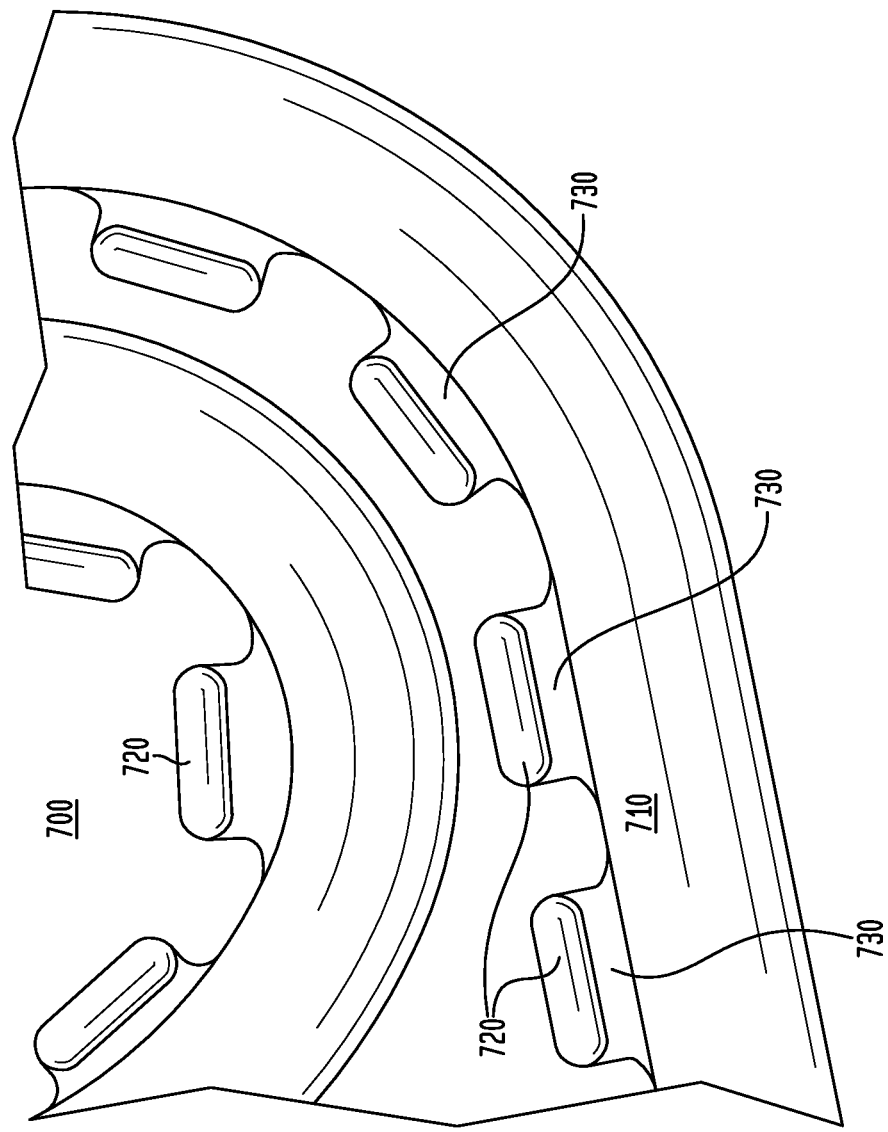
FIG. 7 is a side view of an exemplary embodiment of the present technology.
Figure 8:
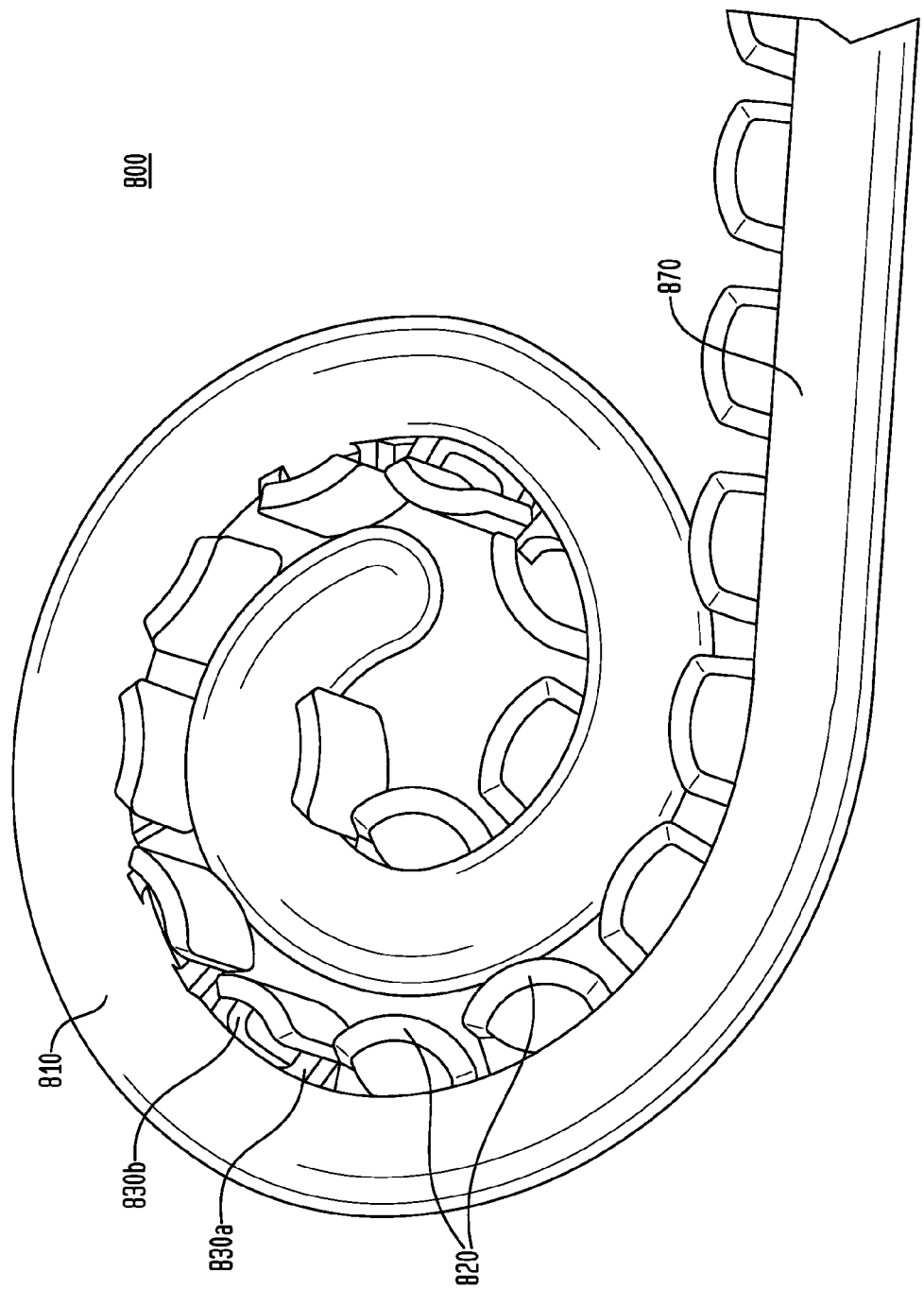
FIG. 8 is a perspective view of an embodiment of the present technology.
Figure 9:
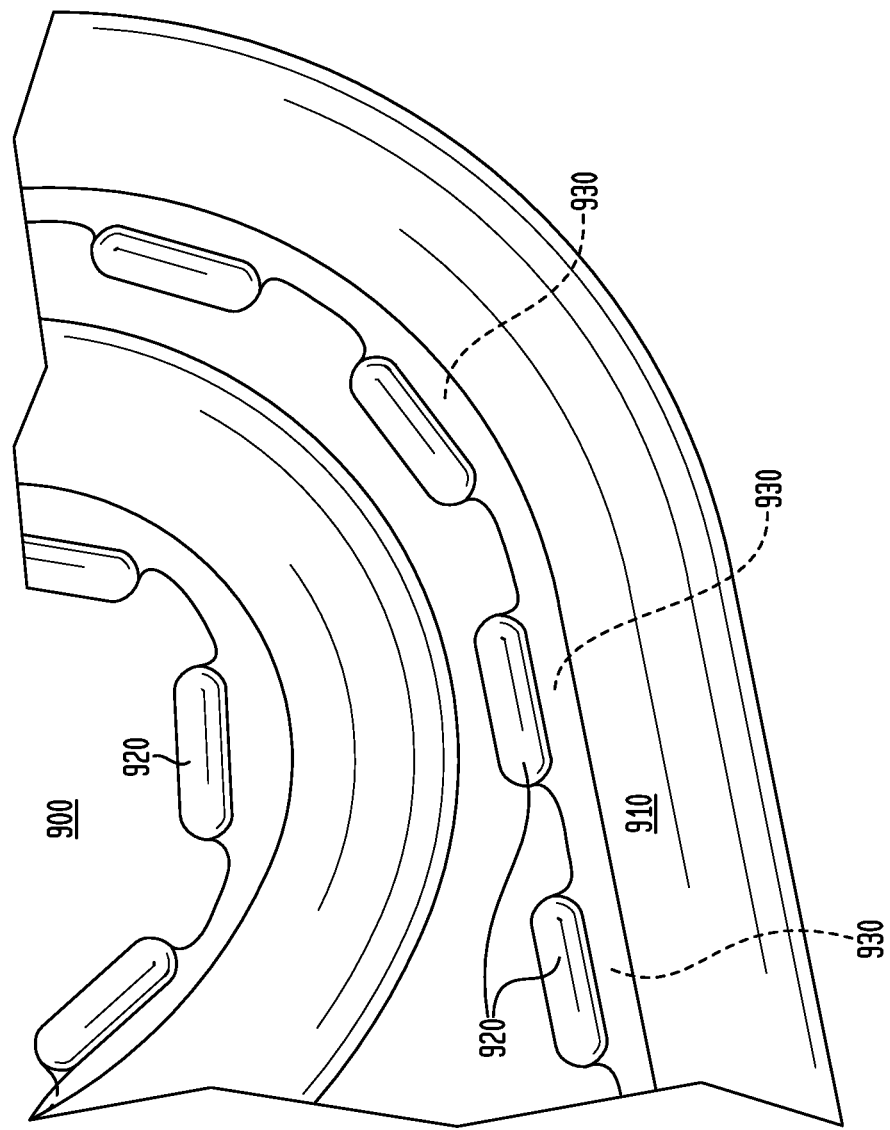
FIG. 9 is a side view of an exemplary embodiment of the present technology.

Referring to FIG. 7, FIG. 8, and FIG. 9, three exemplary embodiments of the present technology are illustrated. In FIG. 7, an partial view of an electrode assembly 700 is shown, depicting several electrode sections, e.g., 720, each connected to a carrier body 710 by a discrete joint, e.g., 730. In FIG. 8, each electrode section, e.g., 820, is connected to the carrier body 810 by a two-part joint, e.g., 830a and 830b. Each of the example embodiments shown in FIG. 7, FIG. 8, and FIG. 9 can be configured to be implanted using one or both of a sleeve insertion tool and a stylet insertion tool or combination. FIG. 9 illustrates a partial view of an electrode assembly 900 is shown, depicting several electrode sections, e.g., 720, each connected to a carrier body 710 by a joint section 730 that is substantially continuous along the longitudinal dimension of the carrier. In other embodiments such as those illustrated by FIG. 7, discontinuities between joint sections can be filled with low durometer medical grade silicone, e.g., to allow for at least semi-independent movement of the joint sections.

In other embodiments of the disclosed technology, the joint sections 330 are discontinuous and one joint section 330 is connected to at least two electrode sections 320. In some embodiments, the number of electrode sections 320 per joint section 330 decreases towards the apical end of the electrode assembly 300. For example, for twenty two (22) electrode contacts 324, the first six (6) basal electrode sections 320 are connected to a first joint section 330, the next five (5) electrode sections 320 are connected to a second joint section 330, the next four (4) electrode sections 320 to a third joint section 330, the next three (3) electrode sections 320 are connected to a fourth joint section 330, the next two (2) electrode sections are connected to a fifth joint section, and last two electrode sections 320 are each connected to a single joint section.

While various embodiments of the present technology have been described above, it should be understood that they have been presented by way of example only, and not limitation. It will be apparent to persons skilled in the relevant art that various changes in form and detail can be made therein without departing from the spirit and scope of the technology. For instance, features described as part of one implementation can be used on another implementation to yield a still further implementation. Thus, the breadth and scope of the present technology should not be limited by any of the above-described exemplary embodiments, but should be defined only in accordance with the following claims and their equivalents. All patents and publications discussed herein are hereby incorporated in their entirety by reference thereto.

What is claimed is:

1. A medical device electrode assembly comprising:
a carrier section;
at least one electrode section comprising:
   an electrode contact; and
   an electrode section body;
a joint section configured to connect the carrier section to the at least one electrode section so as to allow the connected at least one electrode section to move relative to the carrier section; and
a fill section occupying at least a portion of a space between the carrier section and the at least one electrode section that is external to the joint section.

2. The medical device of claim 1, wherein:
the width of the joint section is less than at least one of: the width of the carrier section, and the width of the at least one electrode section.

3. The assembly of claim 1, wherein:
the joint section is configured to provide the connected at least one electrode section with at least one of pitch, roll, and yaw about a point generally along an axis between the carrier section and the at least one electrode section; and
the at least one of pitch, roll, and yaw is created at least in part by a region of the joint section comprising at least one of reduced width of the region with respect to the carrier section and lower durometer of the region with respect to the material of the assembly surrounding the region.

4. The assembly of claim 1, wherein:
the joint section comprises material of durometer less the durometer of each of the carrier section and the at least one electrode section.

5. The assembly of claim 1, wherein:
the joint section comprises material of durometer less the durometer of the carrier section.

6. The assembly of claim 1, wherein the fill section occupies at least a portion of the space between the carrier section and the electrode section that is not occupied by the joint section.

7. The assembly of claim 6, wherein:
the combined width of the joint section and the fill section is less than each of: the width of the carrier section, and the width of the at least one electrode section.

8. The assembly of claim 7, wherein the fill section comprises material of durometer less than the durometer of the joint section.

9. The assembly of claim 1, wherein the carrier section further comprises:
a biasing member biasing the carrier section generally toward the joint section.

10. The assembly of claim 1, wherein:
the carrier section is characterized by a substantially constant diameter along a longitudinal axis of the carrier section.

11. A cochlear implant comprising:
a carrier section;
at least one electrode section comprising:
   an electrode contact; and
   an electrode section body;
a joint section configured to connect the carrier section to the at least one electrode section so as to allow the connected at least one electrode section to move relative to the carrier section; and
a fill section occupying at least a portion of a space between the carrier section and the at least one electrode section that is external to the joint section.

12. The cochlear implant of claim 11, wherein the width of the joint section is less than at least one of: the width of the carrier section, and the width of the at least one electrode section.

13. The cochlear implant of claim 11, wherein:
the joint section is configured to provide the connected at least one electrode section with at least one of pitch, roll, and yaw about a point generally along an axis between the carrier section and the at least one electrode section; and
the at least one of pitch, roll, and yaw is created at least in part by a region of the joint section comprising at least one of reduced width of the region with respect to the carrier section and lower durometer of the region with respect to the material of the assembly surrounding the region.

14. The cochlear implant of claim 11, wherein:
the joint section comprises material of durometer less the durometer of each of the carrier section and the at least one electrode section.

15. The cochlear implant of claim 11, wherein the fill section occupies at least a portion of the space between the carrier section and the electrode section that is not occupied by the joint section.

16. The cochlear implant of claim 15, wherein the combined width of the joint section and the fill section is less than each of: the width of the carrier section, and the width of the at least one electrode section.

17. The cochlear implant of claim 15, wherein the fill section comprises material of durometer less than the durometer of the joint section.

18. The cochlear implant of claim 11, wherein the carrier section further comprises:
a biasing member biasing the carrier section generally toward the joint section.

19. The cochlear implant of claim 11, wherein the carrier section is characterized by a substantially constant diameter along a longitudinal axis of the carrier section.

20. A method of stimulating the tissue of a cochlea using an electrode assembly, the method comprising:
inserting the electrode assembly into the cochlea via at least one of: a cochleostomy, the round window, the oval window, and the promontory or opening in an apical turn of the cochlea; wherein the electrode assembly is configured to stimulate the tissue of the cochlea, the electrode assembly comprising:
  a carrier section;
  at least one electrode section comprising:
    an electrode contact; and
    an electrode section body;
  a joint section configured to connect the carrier section to the at least one electrode section so as to allow the connected at least one electrode section to move relative to the carrier section; and
  a fill section occupying at least a portion of a space between the carrier section and the at least one electrode section that is external to the joint section.

21. The method of claim 20, wherein:
  the width of the joint section is less than at least one of: the width of the carrier section, and the width of the at least one electrode section.

22. The method of claim 20, wherein:
  the joint section is configured to provide the connected at least one electrode section with at least one of pitch, roll, and yaw about a point generally along an axis between the carrier section and the at least one electrode section; and
  the at least one of pitch, roll, and yaw is created at least in part by a region of the joint section comprising at least one of reduced width of the region with respect to the carrier section and lower durometer of the region with respect to the material of the assembly surrounding the region.

23. The method of claim 20 wherein:
  the joint section comprises material of durometer less the durometer of each of the carrier section and the at least one electrode section.

24. The method of claim 20 wherein the fill section occupies at least a portion of the space between the carrier section and the at least one electrode section that is not occupied by the joint section.

25. The method of claim 24, wherein:
  the combined width of the joint section and the fill section is less than each of: the width of the carrier section, and the width of the at least one electrode section.

26. The method of claim 24 wherein:
  the fill section comprises material of durometer less than the durometer of the joint section.

27. The method of claim 20 wherein:
  the carrier section is characterized by a substantially constant diameter along a longitudinal axis of the carrier section.

28. An implantable medical device comprising:
an electrode assembly comprising:
  a carrier section;
  at least one electrode section comprising:
    an electrode contact; and
    an electrode section body;
  means for connecting the carrier section to the at least one electrode section, and allowing the connected at least one electrode section to move relative to the carrier section; and
  a fill section occupying at least a portion of a space between the carrier section and the at least one electrode section that is external to the joint section.

29. The device of claim 28 wherein:
  each of the means for connecting and providing and the carrier section, and the means for connecting and providing comprises material of durometer less the durometer of the carrier section.

30. The device of claim 28 wherein the fill section substantially occupies the space between the carrier section and the electrode section that is not occupied by the means for connecting and providing.

31. The device of claim 30 wherein:
  the fill section comprises material of durometer less than the durometer of the means for connecting and providing.

32. The device of claim 28 wherein:
  the carrier section is characterized by a substantially constant diameter along a longitudinal axis of the carrier section.

33. A medical device electrode assembly comprising:
  a carrier section;
  at least one electrode section comprising:
    an electrode contact, and
    an electrode section body;
  a joint section:
    configured to connect the carrier section to the at least one electrode section; and
    compressible generally along an axis between the carrier section and the at least one electrode section so as to allow the at least one electrode section to move relative to the carrier section; and
  a fill section occupying at least a portion of a space between the carrier section and the at least one electrode section that is external to the joint section.

* * * * *